(12) United States Patent
Yim et al.

(10) Patent No.: US 8,865,934 B2
(45) Date of Patent: Oct. 21, 2014

(54) METHOD FOR PREPARING RAMALIN

(75) Inventors: Joung Han Yim, Gyeonggi-do (KR); Il Chan Kim, Seoul (KR); Sung Gu Lee, Incheon (KR); Dockyu Kim, Incheon (KR); Se Jong Han, Gyeonggi-do (KR); Hyoung Seok Lee, Seoul (KR); Seung Jin Kim, Incheon (KR); Tai Kyoung Kim, Incheon (KR); Pil-Sung Kang, Incheon (KR); Heeyong Park, Gyeonggi-do (KR); Ha Ju Park, Gyeonggi-do (KR); Hye Yeon Koh, Kwangwon-do (KR); Mi Ra Park, Incheon (KR); Yu-Kyeong Park, Incheon (KR)

(73) Assignee: Korea Ocean Research and Development Institute, Incheon (KR)

( * ) Notice: Subject to any disclaimer, the term of this patent is extended or adjusted under 35 U.S.C. 154(b) by 166 days.

(21) Appl. No.: 13/810,145

(22) PCT Filed: Jul. 14, 2011

(86) PCT No.: PCT/KR2011/005206
§ 371 (c)(1),
(2), (4) Date: Apr. 11, 2013

(87) PCT Pub. No.: WO2012/008785
PCT Pub. Date: Jan. 19, 2012

(65) Prior Publication Data
US 2013/0211133 A1    Aug. 15, 2013

(30) Foreign Application Priority Data
Jul. 14, 2010  (KR) .................... 10-2010-0067710

(51) Int. Cl.
C07C 241/00  (2006.01)
C07C 243/00  (2006.01)
C07C 249/00  (2006.01)
C07C 241/04  (2006.01)

(52) U.S. Cl.
CPC .................................. C07C 241/04 (2013.01)
USPC ....................................................... 562/439

(58) Field of Classification Search
None
See application file for complete search history.

(56) References Cited

U.S. PATENT DOCUMENTS
2011/0262374 A1    10/2011 Yim et al.

FOREIGN PATENT DOCUMENTS
KR  10-2010-0052130 A   5/2010
KR  10-2011-0132938 A   12/2011
(Continued)

OTHER PUBLICATIONS
Roullier et al. (Bioorg. Med. Chem. Let., 2010, 20, 4582).*
(Continued)

Primary Examiner — Fereydoun G Sajjadi
Assistant Examiner — Jennifer C Sawyer
(74) Attorney, Agent, or Firm — Hultquist, PLLC; Steven J. Hultquist

(57) ABSTRACT

The present invention relates to a method for synthesizing ramalin, and more particularly to a method for synthesizing ramalin, which comprises allowing 2-hydrazinylphenol to react with L-glutamic acid having a protected carboxyl group at C-1 and a protected amino group at C-2, and a method for preventing decomposition of the ramalin. According to the present invention, ramalin having excellent antioxidant and anti-inflammatory activities can be synthesized in high yield, and thus can be produced in large amounts. In addition, ramalin can be stably maintained for a long period of time, and thus can be easily used for industrial purposes.

9 Claims, 3 Drawing Sheets

(56) References Cited

FOREIGN PATENT DOCUMENTS

WO 2010053327 A2 5/2010
WO 2011152671 A2 12/2011

OTHER PUBLICATIONS

Ahmadjian, V., "The Lichen Symbiosis", 1993, pp. 1-7, Publisher: John Wiley & Sons, Inc., Published in: New York.

Behera, B., et al., "Determination of antioxidative potential of lichen Usnea ghattensis in vitro", "Lebensm. Wiss. Technol. (LWT)", 2006, pp. 80-85, vol. 39.

Bhattarai, H., et al:, "Thin layer chromatography analysis of antioxidant constituents of lichens from Antarctica", "J Nat Med", Jun. 17, 2008, pp. 481-484, vol. 62.

Mueller, K., "Pharmaceutically relevant metabolites from lichens", "Appl Microbiol Biotechnol", May 29, 2001, pp. 9-16, vol. 56.

* cited by examiner

METHOD FOR PREPARING RAMALIN

CROSS-REFERENCE TO RELATED APPLICATIONS

This application is a U.S. national phase under the provisions of 35 U.S.C. §371 of International Patent Application No. PCT/KR11/05206 filed Jul. 14, 2011, which in turn claims priority of Korean Patent Application No. 10-2010-0067710 filed Jul. 14, 2010. The disclosures of such international patent application and Korean priority patent application are hereby incorporated herein by reference in their respective entireties, for all purposes.

TECHNICAL FIELD

The present invention relates to a method for synthesizing ramalin, and more particularly to a method for synthesizing ramalin, which comprises allowing 2-hydrazinylphenol to react with L-glutamic acid having a protected carboxyl group at C-1 and a protected amino group at C-2, and a method for preventing decomposition of the ramalin.

BACKGROUND ART

Lichens are similar to non-flowering plants and refer to the symbiotic association of a fungus (mycobiont) and an alga (photobiont) and/or cyanobacteria. In lichens, the fungus forms a thallus or lichenized stroma that contains characteristic secondary metabolites (Ahmadjin V., *The lichen symbiosis*, Wiley, New York, pp. 1-6, 1993). It is difficult to obtain sufficient amounts of natural lichen samples, and technology of cultivating large amounts of lichens is not known. For this reason, studies on lichens were insufficient compared to studies on higher plants.

As the tissue culture method, mass-production method and biological analysis method for lichens have been improved, studies thereon have been actively conducted (Behera, B. C. et al., *Lebensm. Wiss. Technol.*, 39:805, 2006). Compounds having various biological activities (including cytotoxicity, antifungal, antimicrobial and antioxidant activities), including fatty acids, depsides, depsidones, dibenzofurans, diterpenes, anthraquinones, naphtoquinones, usninic acid, pulvinic acids, xanthones, and epidithiopiperazinediones, have been isolated from lichens (Muller, K., *Appl. Microbiol. Biotechnol.*, 56:9-16, 2001).

*Ramalina terebrata* is a lichen that grows naturally in the Antarctic King George Island and can be easily collected from the King George Island. During studies on the Antarctic lichen *Ramalina terebrata*, the present inventors previously have isolated the novel compound ramalin having excellent antioxidant activity (Korean Patent Laid-Open Publication No. 10-2010-0052130). In addition, it has been reported that ramalin has excellent anti-inflammatory activity (Korean Patent Laid-Open Publication No. 10-2010-0052551).

Because ramalin was confirmed to have excellent antioxidant and anti-inflammatory activities, there is a need to produce ramalin in large amounts. However, a conventional method of isolating ramalin from *Ramalina terebrata* using methanol (Korean Patent Laid-Open Publication No. 10-2010-0052130) entails a problem in that the production of ramalin is expensive and time-consuming, because of the slow growth rate of the polar lichen and because it is difficult to collect a large amount of the polar lichen in nature and the amount of ramalin extracted from *Ramalina terebrata* is very small. Further, ramalin is easily decomposed due to its high antioxidant activity. In addition, ramalin is difficult to maintain, because it is so unstable that more than half thereof disappears within 4 days at room temperature.

L-glutamic acid is a kind of amino acid which has been used as an amino acid-based seasoning, and it is commercially used as a dietary supplement, a nutrition enhancer, a flavor enhancer or the like as a substitute for salt. Thus, L-glutamic acid is inexpensive, can be obtained in large amounts and, at the same time, has optically active sites, like ramalin.

Accordingly, the present inventors have made extensive efforts to develop a method for chemically synthesizing ramalin, and as a result, have found that when L-glutamic acid having optically active sites, like ramalin, is allowed to react with 2-hydrazinylphenol, a ramalin exhibiting the same effects as those of a ramalin derived from a natural material is synthesized, and when the synthesized ramalin is stored together with vitamin C, it is prevented from being decomposed so that it can be maintained for a long period of time, thereby completing the present invention.

DISCLOSURE OF INVENTION

It is an object of the present invention to provide a method for synthesizing ramalin having excellent antioxidant and anti-inflammatory activities, a salt thereof, a solvate thereof, or a solvate of a salt thereof.

Another object of the present invention is to provide a method for preventing decomposition of synthesized ramalin.

To achieve the above objects, the present invention provides a method for synthesizing ramalin represented by the following formula 1, a salt thereof, a solvate thereof, or a solvate of a salt thereof, the method comprising: allowing 2-hydrazinylphenol to react with L-glutamic acid having a protected carboxyl group at C-1 and a protected amino group at C-2, followed by deprotection:

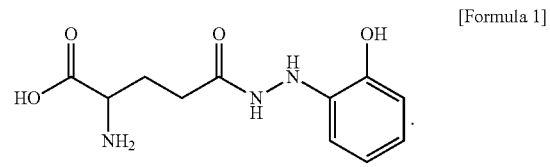 [SMILES: NC(CCC(=O)NNc1ccccc1O)C(=O)O]

[Formula 1]

The present invention also provides a method for preventing decomposition of ramalin, the method comprising maintaining ramalin in a state of being dissolved in a solvent containing vitamin C (L-ascorbic acid).

BEST MODE FOR CARRYING OUT THE INVENTION

Figure 1:
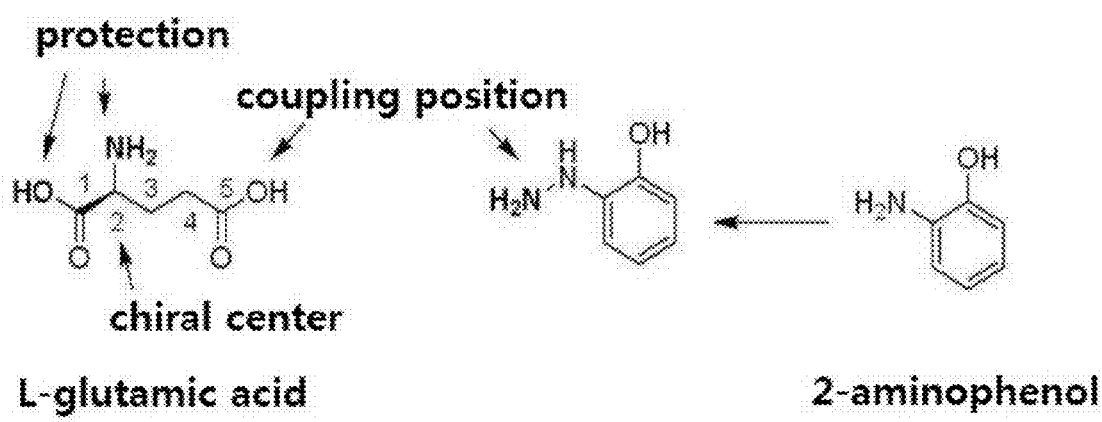
FIG. 1 is a schematic diagram showing reactive sites through which starting materials, L-glutamic acid and 2-hydrazinylphenol, are reacted with each other.

Unless defined otherwise, all technical and scientific terms used herein have the same meaning as commonly understood by one of ordinary skill in the art to which the invention pertains. Generally, the nomenclature used herein are well known and are commonly employed in the art.

In one aspect, the present invention is directed to a method for synthesizing ramalin represented by the following formula 1, a salt thereof, a solvate thereof, or a solvate of a salt thereof, the method comprising: allowing 2-hydrazinylphenol to react with L-glutamic acid having a protected carboxyl group at C-1 and a protected amino group at C-2, followed by deprotection:

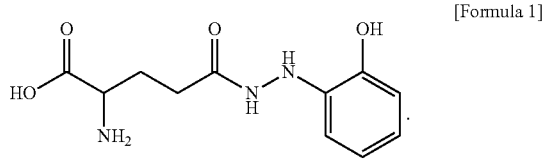 [SMILES: NC(CCC(=O)NNc1ccccc1O)C(=O)O]

[Formula 1]

Ramalin of the present invention is a novel compound, having antioxidant activity, isolated from the Antarctic lichen *Ramalina terebrata*. The high-resolution ES-MS of the ramalin indicated that the ramalin is a compound having a molecular weight of 254.1141 and a molecular formula of $C_{11}H_{16}N_3O_4$ and has the structure shown in formula 1. The name "ramalin" was given because it is a compound isolated from *Ramalina terebrata*.

The present inventors have made efforts to develop a method of chemically synthesizing ramalin instead of isolating and extracting ramalin from *Ramalina terebrata*, and as a result, have found that ramalin is synthesized by allowing 2-hydrazinylphenol to react with L-glutamic acid having a protected carboxyl group at C-1 and a protected amino group at C-2, followed by deprotection.

In the present invention, a salt of the ramalin is not specifically limited as long as it is a pharmacologically acceptable salt. The pharmacologically acceptable salt can be prepared by a conventional method known in the art. For example, the pharmacologically acceptable salt may be a salt of an inorganic acid such as hydrochloric acid, hydrobromic acid, sulfuric acid, sodium hydrogen sulfate, phosphoric acid or carbonic acid; a salt of an organic acid such as formic acid, acetic acid, oxalic acid, benzoic acid, citric acid, tartaric acid, gluconic acid, gestisic acid, fumaric acid, lactobionic acid, salicylic acid or acetylsalicylic acid (aspirin); a metal salt formed by reaction with an alkali metal such as sodium and potassium; or another pharmacologically acceptable salt formed by reaction with an ammonium ion.

As used herein, the term "solvate" refers to a form of the ramalin according to the present invention or a salt thereof, which in solid or liquid state, forms a complex by coordination with solvent molecules. Hydrates are a special form of solvates in which the coordination takes place with water. In the present invention, the solvate is preferably a hydrate.

In the present invention, the starting material 2-hydrazinylphenol may be in tosylate form. The 2-hydrazinylphenol in tosylate form can be prepared by a process comprising the steps of: (a) dissolving 2-aminophenol in methanol and adding hydrochloride gas thereto to obtain 2-aminophenol hydrochloride (HCl); (b) dissolving the 2-aminophenol hydrochloride in ethanol and adding isopentyl nitrite thereto to make a nitramide intermediate; and (c) adding the intermediate to an ethanol solution containing para-toluenesulfonic acid (PTSA or TsOH) and tin chloride ($SnCl_2$), thereby obtaining 2-hydrazinylphenol tosylate.

In a preferred embodiment of the present invention, in step (a), the 2-aminophenol solution may be maintained at a pH of 2-5 while hydrochloride gas is added thereto, and as a result, 2-aminophenol hydrochloride can be obtained in solid form. In step (b), the solution of 2-aminophenol hydrochloride in ethanol may be reacted with isopentyl nitrite at about −5° C. to make the nitramide intermediate. In step (c), the solution of the intermediate in ethanol may be added slowly to the ethanol solution containing para-toluenesulfonic acid (PTSA or TsOH) and tin chloride ($SnCl_2$) at low temperature (−5° C.), thereby obtaining 2-hydrazinylphenol tosylate.

The compounds that are used to prepare 2-hydrazinylphenol tosylate in the present invention are represented by the following formulas: 2-aminophenol (formula 2), 2-aminophenol hydrochloride (formula 3), 2-aminophenol nitramide intermediate (formula 4), and 2-hydrazinylphenol tosylate (formula 5).

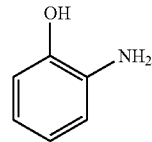

[Formula 2]

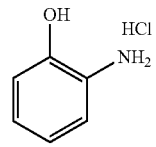

[Formula 3]

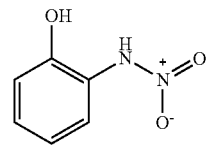

[Formula 4]

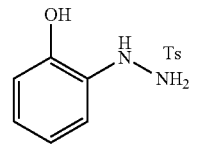

[Formula 5]

In the present invention, L-glutamic acid having a protected carboxyl group at C-1 and a protected amino group at C-2 can be protected using a generally known method for protecting a carboxyl acid and an amino group. For example, the carboxyl group and the amino group can be protected by introducing a benzyl group. However, if the benzyl group is used as the protecting group, it can be introduced not only into C-1 and C-2, but also into the carboxyl group at C-5, and for this reason, a step of removing the benzyl group from the carboxyl group at C-5 is additionally required. In this case, the benzyl group protecting the carboxyl group at C-1 may also be removed, resulting in a decrease in the yield. In addition, the step of removing the protecting group after reaction with 2-hydrazinylphenol may be carried out slowly.

Thus, in a preferred embodiment of the present invention, the L-glutamic acid containing a protected carboxyl group at C-1 and a protected amino group at C-2 may be L-glutamic acid lactone wherein the carboxyl and amino groups are cyclized.

In a more preferred embodiment of the present invention, the L-glutamic acid lacton may be obtained by converting L-glutamic acid into a secondary amine form, followed by cyclization.

If the primary amine form of L-glutamic acid is cyclized, not only C-1, but also C-5 may be cyclized to form a 7-membered ring, suggesting that the desired reaction may not occur.

In one example of the present invention, it was found that, when the reaction of converting L-glutamic acid into a secondary amine form using Troc is carried out using sodium hydrogen carbonate (NaHCO$_3$) for 24 hours, L-glutamic acid lactone can be obtained in a yield of about 85% without a separate purification process.

In another example of the present invention, it was found that a white pure solid primary acid can be obtained by converting L-glutamic acid into a primary acid form using Troc, refluxing the converted L-glutamic acid in toluene with paraformaldehyde in the presence of PTSA (para-toluenesulfonic acid) as an acid catalyst, removing water produced during the reaction, removing the catalyst using potassium carbonate (K$_2$CO$_3$) when water is no longer produced, and recrystallizing the residue from diethyl ether and petroleum ether. The primary acid is L-glutamic acid and may have a structure represented by the following formula 6:

[Formula 6]

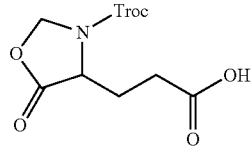

Thus, in the most preferred embodiment of the present invention, the secondary amine form may be prepared by adding 2,2,2-trichloro-ethyl-chloroformate (Troc) to L-glutamic acid and allowing the mixture to react.

In one example of the present invention, it was found that, when L-glutamic acid (primary acid) of formula 6, which contains a protected carboxyl group at C-1 and a protected amino group at C-2, is coupled with 2-hydrazinylphenol after activation of the carboxyl group at C-5, the reaction product is obtained in a yield of 50%.

Thus, in the present invention, L-glutamic acid containing a protected carboxyl group at C-1 and a protected amino group at C-2 preferably has an activated carboxyl group at C-5. For example, the activation of the carboxyl group can be induced by addition of dicyclohexylcarbodiimide (DCC), 1-hydroxybenxotriazole (HOBt), thionyl chloride or ethylchoroformate.

In one example of the present invention, it was found that, when dicyclohexylcarbodiimide (DCC) and 1-hydroxybenxotriazole (HOBt) is used to activate the carboxyl group, a coupling reaction occurs simultaneously with activation, but 2-hydrazinylphenol which is in an unstable state is decomposed, because the reaction time is 20 hours or more. Meanwhile, when thionyl chloride or ethylcholoroformate is used as the activating compound, the reaction yield is 30%. Accordingly, it is preferable to activate the carboxyl group using DCC and HOBt (yield: 50%).

Thus, in the most preferred embodiment of the present invention, L-glutamic acid having a protected carboxyl group at C-1 and a protected amino group at C-2 is treated with dicyclohexylcarbodiimide (DCC) and 1-hydroxybenxotriazole (HOBt) to activate the carboxyl group at C-5 and is additionally treated with triethylamine (TEA).

In one example of the present invention, the protected groups were deprotected using zinc and acetic acid, thereby obtaining ramalin.

Thus, in the present invention, both zinc and acetic acid may be used for deprotection. In addition, any method known in the art may be used for deprotection.

In one example of the present invention, it was found that, when ramalin, which is decomposed within a short time at room temperature due to its high antioxidant activity, is dissolved and maintained in a solvent containing vitamin C, it is maintained for a significantly long period of time.

Thus, in another aspect, the present invention is directed to a method for preventing decomposition of ramalin, the method comprising maintaining ramalin in a state of being dissolved in a solvent containing vitamin C (L-ascorbic acid).

In the present invention, ramalin is dissolved at the same concentration as vitamin C. Preferably, the solvent for dissolving ramalin may be water. More preferably, vitamin C and ramalin may be dissolved in water at a concentration of 1000 ppm.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of Glutamic Acid Having Protected Carboxyl Group at C-1 and Protected Amino Group at C-2 and 2-hydrazinylphenol 1-1: Preparation of Troc-L-glutamic acid As shown in FIG. 1, Troc-L-glutamic acid required for synthesis of ramalin was prepared in the following manner.

In a 500-ml two-neck round flask, 31.5 g (0.375 mol) of NaHCO$_3$ was dissolved in 125 ml of water to make a solution. After the flask was equipped with a reflux condenser and a dropping funnel, 14.7 g (0.1 mol) of L-glutamic acid was added slowly thereto with stirring using a magnetic bar at room temperature. The temperature of the reaction solution was elevated to 35° C., and 2,2,2-trichloroethylchloroflomate was slowly added dropwise thereto. The reaction mixture was heated to 40~45° C. and stirred for 6 hours.

Then, the temperature was lowered to room temperature, after which the reaction mixture continued to stir for about 15 hours. After completion of the reaction, diethylether (30 ml) was added to the reaction solution, the aqueous layer was washed and the organic layer was removed. The aqueous layer was adjusted to a pH of 2 or less by slow addition of 5M HCl, after which it was extracted three time with ethylacetate (EA) (50 ml×3) while the product remaining in the aqueous layer was dissolved out. The EA extract was dried with MgSO$_4$ to remove water and was concentrated in a rotary evaporator. After EA has been completely removed, the title product was obtained as light yellow liquid.

Figure 2:
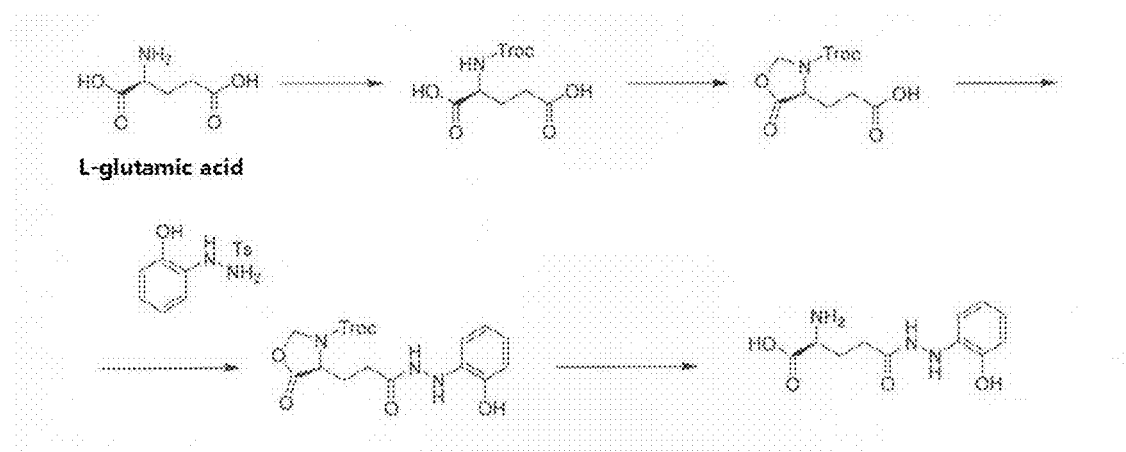
FIG. 2 is a schematic diagram showing one example of a reaction comprising a process of synthesizing ramalin from L-glutamic acid.

As a result, like the compound shown following the first reaction in FIG. 2, Troc-L-glutamic acid protected by N-Troc could be obtained in a high yield of about 85% with high purity without a separate purification process.

In order to determine the structure of the product, NMR spectra (1D and 2D) were recorded in acetone-$d_6$ in addition to $D_2O$ using a JEOL JNM ECP-400 spectrometer (500 MHz for $^1H$ and 500 MHz for $^{13}C$), and chemical shifts were referenced relative to the remaining acetone-$d_6$ ($d_H/d_C$=2.22/21.0). HMQC and HMBC experiments were optimized for $^1J_{CH}$=140 Hz and $^nJ_{CH}$=8 Hz.

$^1H$ NMR (δppm, acetone d6): 1.55-2.75 (m, 4H, $CH_2CH_2$); 4.15-4.55 (m, 1H, CH); 4.70 (s, 2H, $CH_2CCl_3$); 6.65 (d, J 8 Hz, 1H, NH); 10.6 (s, 2H, OH).

1-2: Cyclization

In order to cyclize the protected carboxyl group and amino group of the Troc-L-glutamic acid obtained in Example 1-1, cyclization was carried out in the following manner. In a 500-ml round flask, N-Troc glutamic acid (0.04 mol) was dissolved in toluene (200 ml). The flask was equipped with a Dean-Stark trap and a reflux condenser, after which 2.4 g (0.08 mol) of paraformaldehyde and 0.46 g (0.0024 mol) of PTSA were added to the flask. The reaction temperature was elevated to 120° C., and the reaction mixture was stirred under reflux and heated for about 3 hours until water was no longer produced in the Dean-Stark trap.

After completion of the reaction, the reaction mixture was cooled to room temperature, and 50 ml of EA was added thereto. Then, 4 ml of 0.3M $K_2CO_3$ was added to separate the reaction solution into layers, and the organic layer was separated. The organic layer was washed three times with 5 ml of water and dried with $MgSO_4$ to remove, and the solvent was removed by evaporation. The resulting white solid was washed by addition of 5 ml of ether and 5 ml of petroleum ether.

As a result, like the compound shown following the second reaction in FIG. 2, a white pure solid was obtained in a yield of 85% after filtration and drying. The white solid was found to be N-trichloroethyloxy carbonyl-L-glutamic acid lactone wherein the carbonyl group at C-1 and the amino group at C-2 were protected by cyclization.

In order to determine the structure of the product, NMR spectra (1D and 2D) were recorded in acetone-$d_6$ in addition to $D_2O$ using a JEOL JNM ECP-400 spectrometer (500 MHz for $^1H$ and 500 MHz for $^{13}C$), and chemical shifts were referenced relative to the remaining acetone-$d_6$ ($d_H/d_C$=2.22/21.0). HMQC and HMBC experiments were optimized for $^1J_{CH}$=140 Hz and $^nJ_{CH}$=8 Hz.

$^1H$ NMR (δppm, acetone d6): 2.15-2.65 (m, 4H, $CH_2CH_2$); 4.51 (m, 1H, CH); 4.82-5.00 (m, 2H, $CH_2CCl_3$); 5.37-5.59 (m, 2H, $NCH_2O$); 10.32 (s, 1H, OH).

1-3: Preparation of 2-hydrazinylphenol 2-hydrazinylphenol was prepared in the following manner. In a round flask, 50 g (0.46 mol) of 2-aminophenol was completely dissolved in methanol at room temperature. The solution was stirred for 15 hours or more at a pH of about 2-5 while it was bubbled through a separate HCl gas tube. While the pH was maintained at 2-5, the reaction solution was purged with nitrogen gas for about 30 minutes and then concentrated in a rotary evaporator to obtain a brown solid. The solid was washed with a solution of EA:hexane=3:7, filtered and dried to dryness. The produced solid (2-aminophenol hydrochloride) was collected.

Figure 3:
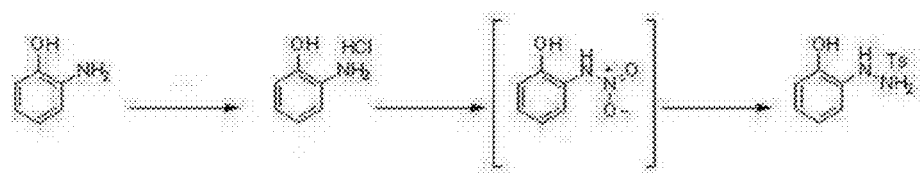
FIG. 3 is a schematic diagram showing one example of a reaction comprising a process of synthesizing 2-hydrazinylphenol from 2-aminophenol.

60 g (0.41 mol) of the collected solid was dissolved completely in 300 ml of ethanol and cooled to −5° C. 55.3 g (0.41 mol) of isopentyl nitrite was diluted in ethanol and added dropwise to the starting solution, followed by stirring for 30 minutes (at −5° C.). In another round flask, 156.3 g (0.82 mol) of tin chloride and 78.4 g (0.41 mol) of PTSA were dissolved in EtOH and cooled to −5° C., and the above aminophenol mixture was added slowly thereto with stirring for 1 hour or more. After completion of the reaction, 500 ml of diethylether was added to the reaction mixture which was then stirred for 10 minutes, and the precipitated solid was filtered. The filter solid was washed with 200 ml of EA and 400 ml of hexane and dried, thereby obtaining 2-hydroxy phenyl hydrazine toluene sulfonic acid salt. FIG. 3 schematically shows this reaction.

As a result, like the compound shown at the end of FIG. 3, 2-hydrazinylphenol was prepared in a yield of about 80%.

In order to determine the structure of the product, NMR spectra (1D and 2D) were recorded in acetone-$d_6$ in addition to $D_2O$ using a JEOL JNM ECP-400 spectrometer (500 MHz for $^1H$ and 500 MHz for $^{13}C$), and chemical shifts were referenced relative to the remaining acetone-$d_6$ ($d_H/d_C$=2.22/21.0). HMQC and HMBC experiments were optimized for $^1J_{CH}$=140 Hz and $^nJ_{CH}$=8 Hz.

$^1H$ NMR (δppm, CD3OD): 2.37 (s, 3H); 6.85 (m, 2H); 7.00 (m, 2H); 7.24 (d, J=10, 2H); 7.71 (d, J=10, 2H).

Example 2

Synthesis of Ramalin 2-1: Coupling of 2-hydrazinylphenol with L-Glutamic Acid Lactone 2-1-1: Coupling with L-Glutamic Acid Lactone Activated by DCC and HOBt 5 g (14.9 mmol) of N-trichloroethyloxy carbonyl-L-glutamic acid lactone prepared in Example 1-2 was dissolved in 80 ml of MC (methylene chloride), and then 4.16 g (5 ml/mmol) of 1.35 eq DCC and 3.03 g of 1.5 eq HOBt ware added thereto, and the mixture was stirred using a magnetic bar. In another flask, 4.9 g (1.2 eq) of 2-hydrazinylphenol tosyl salt (2-hydroxyl phenyl hydrazine tosyl salt) and 2.5 ml of TEA were added to MC and cooled to 0° C. The resulting hydrazine solution was slowly added dropwise to the above starting solution at 0° C. After reaction at 0° C. for 1 hour, the reaction mixture was allowed to react at room temperature for 12 hours. When the reaction was determined to be complete by TLC, the reaction mixture was washed three times with each of 1N HCl, saturated $NaHCO_3$ and brine. The organic layer was separated and dried with $MgSO_4$ to remove water.

As a result, a solvent-free crude product was obtained. It can be used in a subsequent reaction without a purification process. The result of purification indicated that the reaction yield was about 50%.

2-1-2: Coupling with L-Glutamic Lactone Protected by Thionyl Chloride

In a 50-ml flask, 0.01 mol of N-trichloroethyloxy carbonyl-L-glutamic acid lactone prepared in Example 1-2 was dissolved in 2 ml of pure $CCl_4$, and 3.7 ml (0.05 mol) of thionyl chloride was added thereto with stirring. The flask was equipped with a reflux condenser, and the mixture was heated to 70° C. in a water bath. During heating, gas was generated, and the generation of gas was checked using a gas meter or a balloon. When gas was no longer generated, the temperature was lowered to room temperature, and the solvent was completely removed. Pure anhydrous $CH_2Cl_2$ was added to the residue, and the remaining HCl or sulfur dioxide was removed by evaporation.

Next, in a completely dried 100-ml round flask, about 0.01 mol of activated L-glutamic lactone was dissolved in 50 ml of $CH_2Cl_2$. In another flask, 2-hydrazinylphenol tosyl salt (0.0095 mol) and triethylamine (0.0095 mol) were completely dissolved in MC. The resulting hydrazine solution was added slowly to the above starting solution, and pyridine (0.8 mL) was added thereto. The reaction solution was heated at 40° C. for about 3 hours, and then lowered to room temperature and stirred for about 15 hours. Subsequently, the reaction solution was washed with 15 ml of distilled water and 15 ml of $NaHCO_3$ saturated solution, and then washed twice with 15 ml of distilled water. The organic layer was treated with $MgSO_4$ to remove water, after which it was filtered and concentrated, thereby obtaining a crude product.

As a result, it was found that the crude product was obtained in a yield of about 30%.

2-2: Reaction of Obtaining Ramalin by Deprotection

In order to obtain pure ramalin by removing the protecting group from the product of Example 2-1 (that is, N-benzyloxycarbonyl-L-glutamic acid lactone phenyl hydrazine), 790 mg (0.0018 mol) of the product was added to a 100-ml round flask and dissolved in 6 ml of acetic acid. 7 ml of water was added slowly to the solution with stirring using a magnetic bar, and 1 g of zinc powder was added thereto. At about 2 minutes from the time point at which zinc powder was added, the color of the reaction solution became clear. At this time, 5 ml of water was added slowly to the solution which was then stirred for 5 minutes. After 5 minutes, the reaction solution was filtered to remove zinc and was washed twice with 10 ml of MC. The aqueous layer was concentrated and purified by reverse phase column chromatography, thereby obtaining ramalin. FIGS. 1 to 3 schematically show the reactions of Examples 1-1 to 2-2.

By the above reactions, ramalin was obtained in a yield of about 40% (after purification) with a purity of about 99%. The synthesized ramalin was stored at low temperature (−24° C.) in a solid state.

In order to determine the structure of the product, NMR spectra (1D and 2D) were recorded in acetone-$d_6$ in addition to $D_2O$ using a JEOL JNM ECP-400 spectrometer (500 MHz for $^1H$ and 500 MHz for $^{13}C$), and chemical shifts were referenced relative to the remaining acetone-$d_6$ ($d_H/d_C$=2.22/21.0). HMQC and HMBC experiments were optimized for $^1J_{CH}$=140 Hz and $^nJ_{CH}$=8 Hz.

Figure 4:
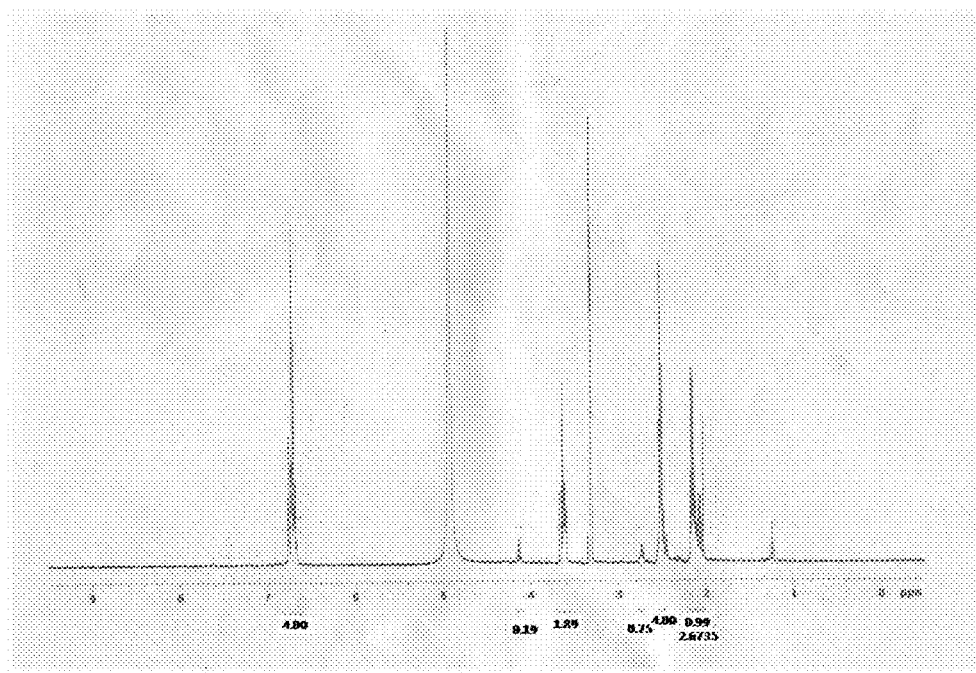
FIG. 4 is a photograph showing the results of $^1$H NMR of synthetic ramalin.

As shown in FIG. 4, the results of NMR analysis of the synthesized ramalin are as follows: $^1H$ NMR (δppm, $CD_3OD$ d6): 2.18 (m, 2H); 2.50 (m, 2H); 3.77 (t, J=6, 1H); 6.85 (m, 4H). Thus, it was found that the structure of the synthesized ramalin was the same as that of a ramalin isolated from a natural material.

Example 3

Examination of Improved Stability of Ramalin by HPLC

Ramalin is easily decomposed due to its high antioxidant activity, and it is so unstable that more than half thereof disappears within 4 days at room temperature. Thus, in order to find a method for maintaining ramalin for a long period of time, ramalin was mixed with vitamin C (L-ascorbic acid) at a ratio of 1:1 (each 1000 ppm) and stored in water at 25° C. and 38° C., and the stability thereof was analyzed.

At varying points of time, 10 μl of a sample was analyzed by semi-preparative reverse phase HPLC using an Agilent Eclipse XDB-C18 column (4.6×150 mm). The solvent system used consisted of 0.1% formic acid-containing water (A line) and 0.1% formic acid-containing methanol (B line). The analysis was carried out for a total of 30 minutes under the following conditions: from 0% to 5% for 15 min, from 5% to 90% for 5 min, from 90% to 0% for 5 min, and finally, from 0% to 5 min. The flow rate was 0.7 ml/min. Then, the change in amount of ramalin was determined by the area value (mAU×S) of HPLC.

Figure 5:
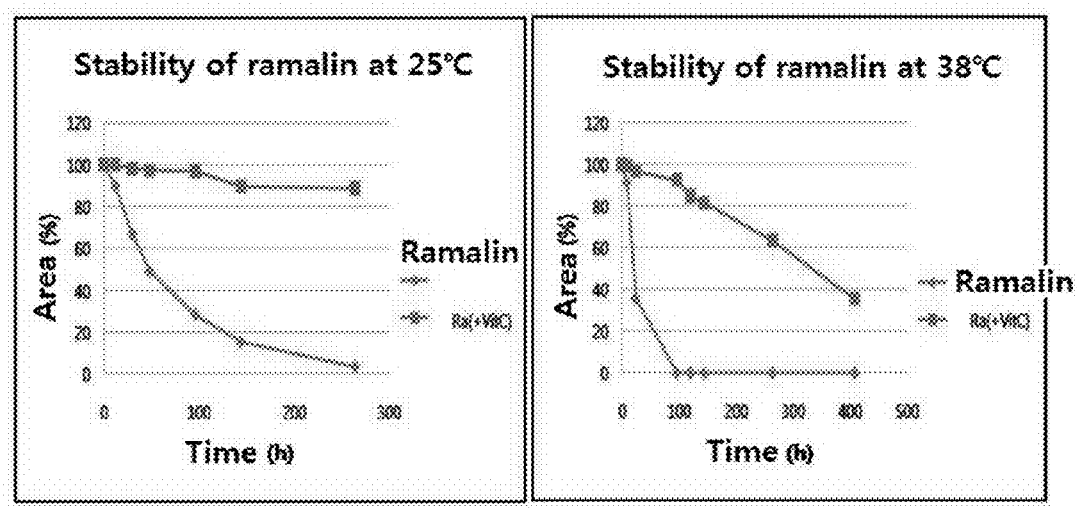
FIG. 5 is a set of graphs showing the results of measuring the preserved amount of ramalin as a function of maintenance time at 25° C. and 38° C.

As a result, as can be seen in FIG. 5, ramalin alone was decomposed rapidly with the passage of time. However, when ramalin and vitamin C (L-ascorbic acid) were mixed at a ratio of 1:1 (each 1000 ppm) and stored in water, the stability of the ramalin was maintained. In addition, when ramalin was stored together with vitamin C, it was somewhat stable even at 38° C. at which ramalin stored alone would completely disappear. In other words, at 38° C., vitamin C broken out in advance, and then ramalin started to disappear, and after about 200 hours (vitamin C almost disappeared), ramalin was somewhat stable.

Example 4

Comparison of Antioxidant Activity Between Natural Material-Derived Ramalin and Synthetic Ramalin In order to compare the antioxidant activity of the synthetic ramalin with that of natural material-derived ramalin, the activities of the ramalins against 2,2-di(4-tert-octylphenyl)-1-picrylhydrazyl (DPPH) free radicals was measured. Butylated hydroxyl anisole (BHA) was used as a control. In addition, the compounds used in the measurement of this experiment all had a purity of 98% or more.

Specifically, 1.5 ml of each of natural material-derived ramalin, synthetic ramalin and the control BHA, dissolved in methanol at various concentrations (0.1-3.0 ug/ml), was mixed with 0.5 ml of 0.1 mM DPPH dissolved in the same solvent. The mixture was allowed to react at room temperature for 30 minutes in the absence of light, and then the absorbance at 517 nm was measured using an UV-visible spectrophotometer (SCINCO, Korea). As blank, a reaction product between 0.5 ml of 0.1 mM DPPH and 1.5 ml of methanol was used. Electron donating ability (DEA) was calculated using the following equation:

$$\text{Electron donating ability (DEA) \%} = \{1-(S/B)\} \times 100$$

wherein S is the absorbance at 517 nm of the reaction product between DPPH and the sample, and B is the absorbance at 517 nm of the reaction product between DPPH and methanol.

Figure 6:
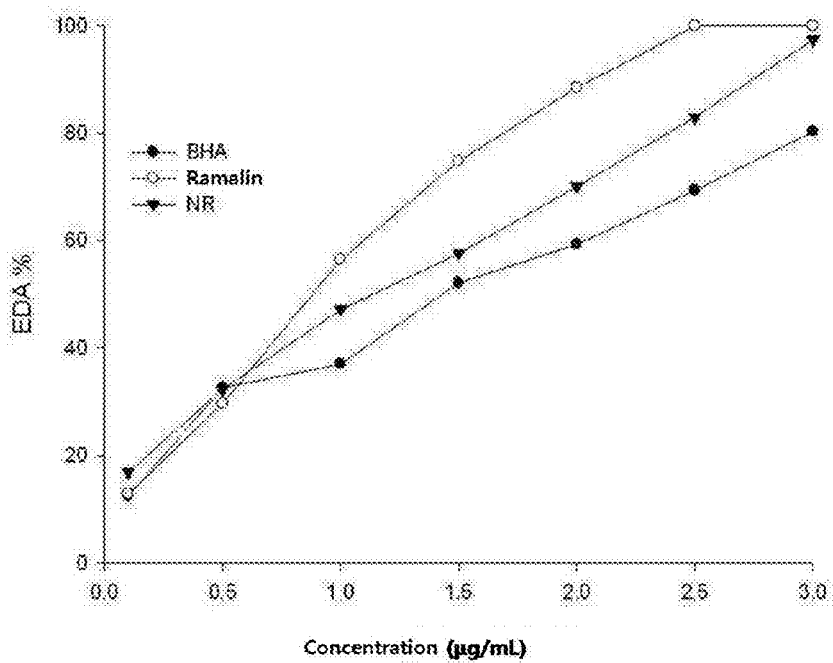
FIG. 6 is a graph showing a comparison of antioxidant activity between synthetic ramalin and natural material-derived ramalin.

As a result, as can be seen in FIG. 6 and Table 1 below, the $IC_{50}$ value of the natural material-derived ramalin was 1.22 μg/ml, and the $IC_{50}$ value of the synthetic ramalin was 0.96 μg/ml, suggesting that the natural material-derived ramalin and the synthetic ramalin have almost similar antioxidant activities.

TABLE 1

| Compounds | IC$_{50}$ values (μg/ml) |
|---|---|
| Synthesized ramalin | 0.96 |
| Butylated hydroxyl anisole (BHA) as a control | 1.43 |
| Natural material-derived ramalin | 1.22 |

INDUSTRIAL APPLICABILITY

As described above, according to the present invention, ramalin having excellent antioxidant and anti-inflammatory activities can be synthesized in high yield, and thus can be produced in large amounts. In addition, ramalin can be stably maintained for a long period of time, and thus can be easily used for industrial purposes.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for synthesizing ramalin of formula 1, a salt thereof, a solvate thereof, or a solvate of a salt thereof, the method comprising: allowing 2-hydrazinylphenol to react with L-glutamic acid having a protected carboxyl group at C-1 and a protected amino group at C-2, followed by deprotection:

[Formula 1]

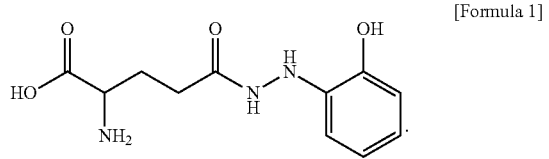 [SMILES: NC(CCC(=O)NNc1ccccc1O)C(=O)O]

2. The method of claim 1, wherein the 2-hydrazinylphenol is in tosylate form.

3. The method of claim 2, wherein the 2-hydrazinylphenol in tosylate form is prepared by a process comprising the steps of:
   (a) dissolving 2-aminophenol in methanol and adding hydrochloride gas thereto to obtain 2-aminophenol hydrochloride (HCl);
   (b) dissolving the 2-aminophenol hydrochloride in ethanol and adding isopentyl nitrite thereto to make a nitramide intermediate; and
   (c) adding the intermediate to an ethanol solution containing para-toluenesulfonic acid (PTSA or TsOH) and tin chloride (SnCl$_2$), thereby obtaining 2-hydrazinylphenol tosylate.

4. The method of claim 1, wherein the L-glutamic acid containing a protected carboxyl group at C-1 and a protected amino group at C-2 is L-glutamic acid lactone wherein the carboxyl and amino groups are cyclized.

5. The method of claim 4, wherein the L-glutamic acid lacton is obtained by converting L-glutamic acid into a secondary amine form, followed by cyclization.

6. The method of claim 5, wherein the secondary amine form is prepared by adding 2,2,2-trichloro-ethyl-chloroformate (Troc) to L-glutamic acid and allowing the mixture to react.

7. The method of claim 1, wherein the L-glutamic acid containing a protected carboxyl group at C-1 and a protected amino group at C-2 has an activated carboxyl group at C-5.

8. The method of claim 7, wherein the carboxyl group at C-5 is activated by treating the L-glutamic acid with dicyclohexylcarbodiimide (DCC) and 1-hydroxybenxotriazole (HOBt).

9. The method of claim 8, wherein the carboxyl group at C-5 is activated by additionally treating the L-glutamic acid with triethylamine (TEA).

* * * * *